(12) United States Patent
Bhadri et al.

(10) Patent No.: US 8,172,834 B2
(45) Date of Patent: May 8, 2012

(54) PORTABLE HANDHELD ILLUMINATION SYSTEM

(75) Inventors: Prashant R. Bhadri, Pico Rivera, CA (US); Charles DeBoer, Pasadena, CA (US); Matthew McCormick, Forest Falls, CA (US); Ralph Kerns, Laguna Niguel, CA (US); Aaron Barnes, Washington, DC (US); Mark S. Humayun, Glendale, CA (US); Jaw-Chyng Lormen Lue, San Gabriel, CA (US)

(73) Assignee: Doheny Eye Institute, Los Angeles, CA (US)

( * ) Notice: Subject to any disclaimer, the term of this patent is extended or adjusted under 35 U.S.C. 154(b) by 701 days.

(21) Appl. No.: 12/237,110

(22) Filed: Sep. 24, 2008

(65) Prior Publication Data
US 2009/0146583 A1  Jun. 11, 2009

Related U.S. Application Data

(63) Continuation of application No. 12/039,298, filed on Feb. 28, 2008, now abandoned.

(60) Provisional application No. 60/892,028, filed on Feb. 28, 2007.

(51) Int. Cl.
*H05B 37/00* (2006.01)

(52) U.S. Cl. .......................................... 606/2; 315/149

(58) Field of Classification Search .................. 362/800, 362/552, 555; 600/132, 109; 315/149, 158, 315/156, 159, 157; 606/2
See application file for complete search history.

(56) References Cited

U.S. PATENT DOCUMENTS

| | | |
|---|---|---|
| 3,775,606 A | 11/1973 | Bazell et al. |
| 3,798,435 A | 3/1974 | Schindl |
| 4,196,460 A | 4/1980 | Schreckendgust |
| 4,651,257 A | 3/1987 | Gehly |
| 5,115,124 A | 5/1992 | Muto et al. |
| 5,147,354 A | 9/1992 | Boutacoff et al. |
| 5,219,444 A | 6/1993 | Chiaramonte et al. |
| 5,419,323 A | 5/1995 | Kittrell et al. |

(Continued)

FOREIGN PATENT DOCUMENTS

CN 1828128 A 9/2006

(Continued)

OTHER PUBLICATIONS

International Search Report for related PCT Application No. PCT/US08/55277, Jul. 28, 2008.

(Continued)

*Primary Examiner* — David Hung Vu
(74) *Attorney, Agent, or Firm* — Knobbe, Martens, Olson & Bear, LLP

(57) ABSTRACT

Illumination systems are described that can include one or more light sources, which can include LEDs, one or more lenses, and one or more optical fibers. A handheld, portable, and surgical intraocular illumination system is disclosed that is disposable, low-cost, and efficient. A surgeon can have direct control of turning the illuminator on and off and adjusting the intensity via a simple control ergonomically placed on the handpiece and/or voice activated control. A coupling is provided, such as through an endo-probe, which is coupled to the one or more light sources. A user input device can be included that is operable to transmit to a feedback controller a first signal based on a user-selected light intensity. The feedback controller can, in response to the first signal, transmit a second signal to the power source for altering the power provided by the power source to the illumination system.

15 Claims, 7 Drawing Sheets

U.S. PATENT DOCUMENTS

| | | | |
|---|---|---|---|
| 5,421,337 A | 6/1995 | Richards-Kortum et al. |
| 5,422,792 A | 6/1995 | Neumann |
| 5,562,100 A | 10/1996 | Kittrell et al. |
| 5,570,698 A | 11/1996 | Liang et al. |
| 5,612,540 A | 3/1997 | Richards-Kortum et al. |
| 5,634,711 A | 6/1997 | Kennedy et al. |
| 5,697,373 A | 12/1997 | Richards-Kortum et al. |
| 5,699,795 A | 12/1997 | Richards-Kortum et al. |
| 5,733,739 A | 3/1998 | Zakim et al. |
| 5,818,052 A | 10/1998 | Elabd |
| 5,842,995 A | 12/1998 | Mahadevan-Jansen et al. |
| 5,918,973 A | 7/1999 | Nojiri |
| 5,920,399 A | 7/1999 | Sandison et al. |
| 5,993,001 A | 11/1999 | Bursell et al. |
| 6,016,038 A | 1/2000 | Mueller et al. |
| 6,135,965 A | 10/2000 | Tumer et al. |
| 6,150,774 A | 11/2000 | Mueller et al. |
| 6,160,835 A | 12/2000 | Kwon |
| 6,166,496 A | 12/2000 | Lys et al. |
| 6,178,346 B1 | 1/2001 | Amundson et al. |
| 6,183,086 B1 | 2/2001 | Neubert |
| 6,211,626 B1 | 4/2001 | Lys et al. |
| 6,230,046 B1 | 5/2001 | Crane et al. |
| 6,270,491 B1 | 8/2001 | Toth et al. |
| 6,280,059 B1 | 8/2001 | Ito et al. |
| 6,292,901 B1 | 9/2001 | Lys et al. |
| 6,340,868 B1 | 1/2002 | Lys et al. |
| 6,357,877 B2 | 3/2002 | Takada |
| D457,667 S | 5/2002 | Piepgras et al. |
| D457,669 S | 5/2002 | Piepgras et al. |
| D457,974 S | 5/2002 | Piepgras et al. |
| D458,395 S | 6/2002 | Piepgras et al. |
| 6,425,677 B1 | 7/2002 | Chuang |
| 6,436,035 B1 | 8/2002 | Toth et al. |
| D463,610 S | 9/2002 | Piepgras et al. |
| 6,459,919 B1 | 10/2002 | Lys et al. |
| D468,035 S | 12/2002 | Blanc et al. |
| 6,513,962 B1 | 2/2003 | Mayshack et al. |
| 6,528,954 B1 | 3/2003 | Lys et al. |
| 6,539,942 B2 | 4/2003 | Schwartz et al. |
| 6,540,390 B2 | 4/2003 | Toth et al. |
| 6,548,967 B1 | 4/2003 | Dowling et al. |
| 6,577,080 B2 | 6/2003 | Lys et al. |
| 6,593,101 B2 | 7/2003 | Richards-Kortum et al. |
| 6,608,453 B2 | 8/2003 | Morgan et al. |
| 6,624,597 B2 | 9/2003 | Dowling et al. |
| 6,639,674 B2 | 10/2003 | Sokolov et al. |
| 6,652,452 B1 | 11/2003 | Seifert et al. |
| 6,685,730 B2 | 2/2004 | West et al. |
| 6,717,376 B2 | 4/2004 | Lys et al. |
| 6,720,745 B2 | 4/2004 | Lys et al. |
| D491,678 S | 6/2004 | Piepgras |
| D492,042 S | 6/2004 | Piepgras |
| 6,766,184 B2 | 7/2004 | Utzinger et al. |
| 6,774,584 B2 | 8/2004 | Lys et al. |
| 6,777,891 B2 | 8/2004 | Lys et al. |
| 6,781,329 B2 | 8/2004 | Mueller et al. |
| 6,786,628 B2 | 9/2004 | Steen et al. |
| 6,788,011 B2 | 9/2004 | Mueller et al. |
| 6,824,294 B2 | 11/2004 | Cao |
| 6,886,964 B2 | 5/2005 | Gardiner et al. |
| 6,934,576 B2 | 8/2005 | Camacho et al. |
| 6,964,490 B2 | 11/2005 | Scholz |
| 6,965,205 B2 | 11/2005 | Piepgras et al. |
| 6,967,448 B2 | 11/2005 | Morgan et al. |
| 6,975,079 B2 | 12/2005 | Lys et al. |
| 7,014,336 B1 | 3/2006 | Ducharme et al. |
| 7,020,370 B2 | 3/2006 | Harris |
| 7,038,398 B1 | 5/2006 | Lys et al. |
| 7,048,379 B2 | 5/2006 | Miller et al. |
| 7,063,436 B2 | 6/2006 | Steen et al. |
| 7,064,498 B2 | 6/2006 | Dowling et al. |
| 7,116,437 B2 | 10/2006 | Weinstein et al. |
| 7,130,115 B2 | 10/2006 | Olszak et al. |
| 7,132,785 B2 | 11/2006 | Ducharme |
| 7,161,311 B2 | 1/2007 | Mueller et al. |
| 7,161,313 B2 | 1/2007 | Piepgras et al. |
| 7,174,094 B2 | 2/2007 | Steinkamp |
| 7,184,610 B2 | 2/2007 | Weinstein et al. |
| 7,186,003 B2 | 3/2007 | Dowling et al. |
| 7,229,202 B2 | 6/2007 | Sander |
| 7,236,815 B2 | 6/2007 | Richards-Kortum et al. |
| 7,245,273 B2 | 7/2007 | Eberl et al. |
| 7,255,457 B2 | 8/2007 | Ducharme et al. |
| 7,270,439 B2 | 9/2007 | Horrell et al. |
| 7,284,861 B2 | 10/2007 | Fujieda |
| 7,308,296 B2 | 12/2007 | Lys et al. |
| 7,311,401 B2 | 12/2007 | Goldfain et al. |
| 7,365,844 B2 | 4/2008 | Richards-Kortum et al. |
| 7,387,405 B2 | 6/2008 | Ducharme et al. |
| 7,420,153 B2 | 9/2008 | Palmer et al. |
| 7,422,327 B2 | 9/2008 | Smith |
| 7,458,375 B2 | 12/2008 | Schwartz et al. |
| 7,488,088 B2 | 2/2009 | Brukilacchio |
| 7,488,101 B2 | 2/2009 | Brukilacchio |
| 7,499,634 B2 | 3/2009 | Yogesan et al. |
| 7,572,028 B2 | 8/2009 | Mueller et al. |
| 7,614,763 B2 | 11/2009 | Leibinger et al. |
| 7,625,098 B2 | 12/2009 | Rains, Jr. et al. |
| 7,652,772 B2 | 1/2010 | Backman et al. |
| 7,654,716 B1 | 2/2010 | Bhadri et al. |
| 7,658,708 B2 | 2/2010 | Schwartz et al. |
| 7,677,730 B2 | 3/2010 | Shimizu |
| 7,710,007 B2 | 5/2010 | Liang |
| 7,731,387 B2 | 6/2010 | Cortenraad et al. |
| 7,762,664 B2 | 7/2010 | Fink |
| 7,772,534 B2 | 8/2010 | Ito |
| 7,801,590 B2 | 9/2010 | Feldman et al. |
| 7,845,823 B2 | 12/2010 | Mueller et al. |
| 7,850,334 B2 | 12/2010 | Holder et al. |
| 2002/0025298 A1 | 2/2002 | Blumenkranz et al. |
| 2002/0101568 A1 | 8/2002 | Eberl et al. |
| 2003/0103262 A1 | 6/2003 | Descour et al. |
| 2003/0112639 A1 | 6/2003 | Stack |
| 2003/0218755 A1 | 11/2003 | Wei et al. |
| 2004/0023415 A1 | 2/2004 | Sokolov et al. |
| 2004/0032750 A1 | 2/2004 | Watts et al. |
| 2004/0064053 A1 | 4/2004 | Chang et al. |
| 2004/0090796 A1 | 5/2004 | Steen et al. |
| 2004/0181133 A1 | 9/2004 | Al-Ali |
| 2005/0075628 A1 | 4/2005 | Cazzini et al. |
| 2005/0099824 A1 | 5/2005 | Dowling et al. |
| 2005/0157263 A1 | 7/2005 | Sakata et al. |
| 2005/0182321 A1 | 8/2005 | Frangioni |
| 2005/0222499 A1 | 10/2005 | Banik et al. |
| 2006/0134001 A1 | 6/2006 | Frangioni |
| 2006/0152172 A9 | 7/2006 | Mueller et al. |
| 2006/0228256 A1 | 10/2006 | McDevitt et al. |
| 2006/0257941 A1 | 11/2006 | McDevitt et al. |
| 2006/0257991 A1 | 11/2006 | McDevitt et al. |
| 2006/0257992 A1 | 11/2006 | McDevitt et al. |
| 2006/0257993 A1 | 11/2006 | McDevitt et al. |
| 2006/0282064 A1 | 12/2006 | Shimizu et al. |
| 2007/0038121 A1 | 2/2007 | Feldman et al. |
| 2007/0115658 A1 | 5/2007 | Mueller et al. |
| 2007/0173718 A1 | 7/2007 | Richards-Kortum et al. |
| 2007/0244367 A1 | 10/2007 | Caffey et al. |
| 2008/0029708 A1 | 2/2008 | Olsen et al. |
| 2008/0038738 A1 | 2/2008 | Weigum et al. |
| 2008/0051629 A1 | 2/2008 | Sugiyama et al. |
| 2008/0095714 A1 | 4/2008 | Castella et al. |
| 2008/0200761 A1 | 8/2008 | Schwartz et al. |
| 2008/0208000 A1 | 8/2008 | Schwartz et al. |
| 2008/0308098 A1 | 12/2008 | Schwartz et al. |
| 2009/0009759 A1 | 1/2009 | Backman et al. |
| 2009/0016075 A1 | 1/2009 | Bhadri et al. |
| 2009/0068108 A1 | 3/2009 | Sokolov et al. |
| 2009/0237920 A1 | 9/2009 | Dallas et al. |
| 2010/0002428 A1 | 1/2010 | Hall et al. |
| 2010/0026957 A1 | 2/2010 | Tanguay, Jr. et al. |
| 2010/0093561 A1 | 4/2010 | Rantala et al. |
| 2010/0095969 A1 | 4/2010 | Schwartz et al. |
| 2010/0137687 A1 | 6/2010 | Schwartz et al. |
| 2010/0157620 A1 | 6/2010 | Bhadri et al. |
| 2010/0210951 A1 | 8/2010 | Rahman et al. |

| | | |
|---|---|---|
| 2010/0262017 A1 | 10/2010 | Frangioni |
| 2010/0262020 A1 | 10/2010 | Backman et al. |
| 2010/0321772 A1 | 12/2010 | Reimer et al. |

FOREIGN PATENT DOCUMENTS

| | | |
|---|---|---|
| WO | WO2005/081914 | 9/2005 |
| WO | WO2008/106590 | 9/2008 |

OTHER PUBLICATIONS

Written Opinion for related PCT Application No. PCT/US08/55277, Jul. 28, 2008.

International Search Report and Written Opinion for PCT Application No. PCT/US05/05521 mailed on Jan. 24, 2008.

International Search Report and Written Opinion for Related PCT Application No. PCT/US08/55277 mailed on Jul. 28, 2008.

International Search Report for PCT Application U.S. Appl. No. PCT/US09/41723 mailed Oct. 2, 2009.

U.S. Appl. No. 12/641,269, filed Jun. 24, 2010, Bhadri et al.

Everdell, et al., "Improving Ocular Disease Screening by LED Illumination of the Eye"; Medical News Today; press release available online at http://www.medicalnewstoday.com/articles/199575.php on Sep. 1, 2010.

International Preliminary Report on Patentability dated Feb. 24, 2009 for PCT Application No. PCT/US05/05521 filed Feb. 22, 2005.

International Preliminary Report on Patentability dated Sep. 1, 2009 for PCT Application No. PCT/US08/55277 filed Feb. 28, 2008.

International Search Report and Written Opinion dated Oct. 2, 2009 for PCT Application Serial No. PCT/US09/41723.

PORTABLE HANDHELD ILLUMINATION SYSTEM

RELATED APPLICATION

This application is a continuation of U.S. application Ser. No. 12/039,298 filed 28 Feb. 2008, now abandoned; and also claims the benefit of U.S. Provisional Patent Application No. 60/892,028 filed 28 Feb. 2007, the entire contents of which are incorporated herein by reference.

BACKGROUND

Prior art surgical lighting techniques, including applications of light sources in ophthalmology surgery, have utilized tungsten halogen, metal halide, xenon arc, etc. Such surgical lighting techniques can present a number of limitations. For example, halogen bulbs suffer from relatively low efficiency, poor reliability, considerable generation of heat, and a relatively short lifetime.

Moreover, because of packaging limitations, the light for such prior art lighting has typically required use of fiber optics for delivery from the peripheral illumination source to the inside of the eye, considerable resultant light loss. Such packaging limitations have also contributed to bulky, expensive, and inconvenient lighting, that has often exhibited poor robustness, e.g., has been susceptible to system vibrations, dirt, and moisture.

What is desirable, therefore, are surgical lighting techniques that address the noted limitations of prior art surgical lighting techniques. What is further desirable are surgical lighting techniques that can be utilized for surgeries on the eye and related physical structures.

SUMMARY

Embodiments and aspects of the present disclosure address limitations of the prior art by utilizing configurations of light sources in conjunction with a corresponding power supply, a handheld device, and fiber optics for delivery of light at desired wavelengths to a surgical site. Light Emitting Diodes (also known as "LED"s) can be used as light sources in exemplary embodiments. Embodiments of an illumination system according to the present disclosure can further include one or more lenses and/or filters for selecting one or more specific wavelengths or wavelength ranges from the optical output of the light source(s).

An aspect of the present disclosure is directed to an illumination system including a handheld, untethered, portable, and complete surgical intraocular illumination system utilizing one or more LEDs as light sources. Such systems can accordingly be disposable, low-cost, and energy efficient. By use of such systems, a surgeon can have direct control of turning the illuminator on and off and adjusting the intensity by way of a simple control ergonomically placed on the handpiece and/or voice activated control. The handheld system can be incorporated in an injection molded housing structure. An energy supply component/system, e.g., a battery, can be included to provide power to the illumination system. The system can include an electronic system that includes a microprocessor and related circuitry that generates current pulses for the LEDs. In addition, the circuitry can consists of a converter, e.g., a boost converter, to power the LEDs. A coupling can provided through a probe, e.g., an endo-probe, which can be coupled to the LED(s).

According to an embodiment of the present disclosure, an illumination system can include a host system and a portable handpiece communicating with the host system over a wired communication protocol. The host system can include a power source and a feedback controller. The portable handpiece an include an illumination system that emits light responsive to power received from the power source. The illumination system is preferably implemented via light emitting diodes (LEDs). The portable handpiece can also include a user input device for controlling intensity of light emitted by the illumination system. The user input device can transmit to the feedback controller a first signal based on a user-selected light intensity. The feedback controller can transmit in response to the first signal, a second signal to the power source for altering the power provided by the power source to the illumination system.

According to a further embodiment of the present disclosure, an illumination system can include a host system and a portable handpiece communicating with the host system over a wireless communication protocol. According to this embodiment, the host system can include a first transceiver adhering to a wireless communication protocol and a voice recognition system. The portable handpiece can include a second transceiver for wireless communication with the host system, a power source, a feedback controller, and an illumination system emitting light responsive to power received from the power source. A first user input device can control intensity of the light emitted by the illumination system. The first user input device transmits to the feedback controller a first signal based on a user-selected light intensity. The feedback controller transmits in response to the first signal, a second signal to the power source for altering the power provided by the power source to the illumination system. The handpiece can also include a second user input device for receiving voice data provided by the user. The voice data is wirelessly transmitted by the second transceiver to the first transceiver and processed by the voice recognition system for storing or generating an output in response.

According to further embodiments, the handheld illumination device may serve as potential light source for other illuminated instruments beside vitrectomy intraocular illumination, such as, for example, indirect opthalmoscope, direct opthalmoscope, slit lamp, and fundus camera, etc.

Other aspects, embodiments, and details of the of present disclosure will be apparent from the following description when read together with the accompanying drawings.

BRIEF DESCRIPTION OF FIGURES

Aspects of the present disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings.

Figure 1:
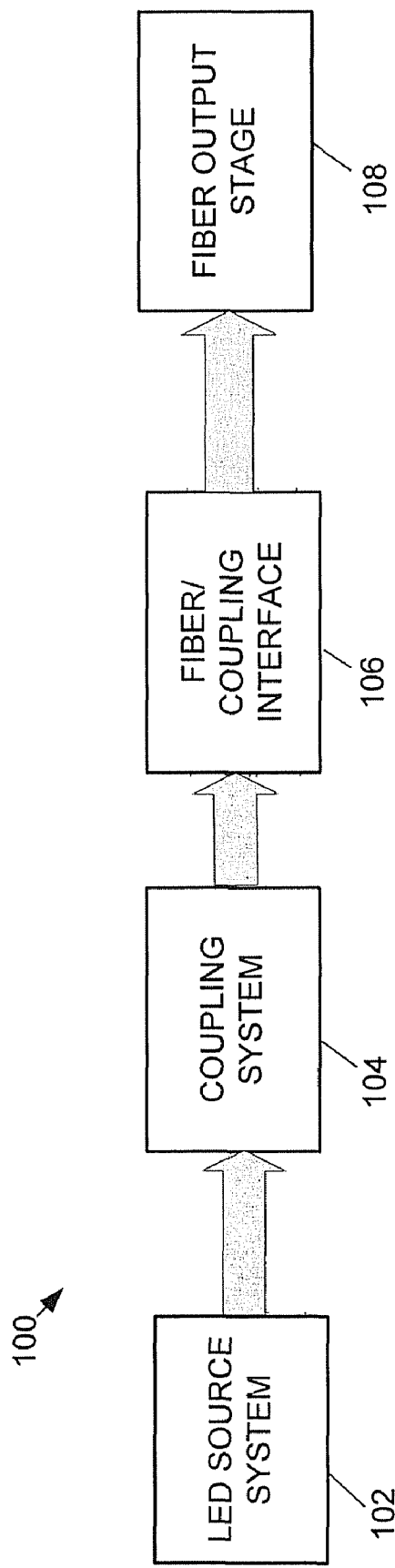
FIG. 1 is a schematic view of a system level representation of a portion of a handheld illumination system according to an embodiment of the present disclosure.

It should be understood by one skilled in the art that the embodiments depicted in the drawings are illustrative and variations of those shown as well as other embodiments described herein may be envisioned and practiced within the scope of the disclosure.

DETAILED DESCRIPTION

Aspects and embodiments of the present disclosure are directed to and can provide illumination systems, and related techniques/methods, utilizing a handheld surgical, e.g., intraocular, illumination system with one or more light sources. Such handheld illumination systems can be portable and/or include portable components. Exemplary embodiments according to the present disclosure provide light sources including one or more light emitting diodes (also known as LED's).

Such handheld systems may be used as or included with an endo-probe, useful for surgical procedures including those performed on the eye. Such systems can include feedback functionality allowing a surgeon/operator to adjust light output, and may be disposable, low-cost, and energy efficient. By use of such systems, a surgeon can have direct control of turning an illuminator of the system on and off and adjusting the light intensity by way of a simple control ergonomically placed on the handpiece and/or voice activated control.

LED light sources used in/for embodiments of the present disclosure can provide various advantages. As they are based on electronic component design, LEDs are largely if not entirely immune from or resistant to system vibrations. LEDs can be protected from dirt and moisture, facilitating useful lifetimes that can increase to or approach thousands of hours, which is much higher than a non-LED light source. Further, LED-based light sources can operate at lower temperatures, and therefore have lower heat dissipation requirement, thereby eliminating complex heat sink systems commonly used for prior art lighting techniques. Cost of a single LED system is exponentially less expensive than a stand light source system because of the simple packaging. Additionally, LEDs are available in multiple colors/including high output efficiency.

LED-based systems according to the present disclosure can offer improved surgeon controlled surgical instruments that can provide lighting that is either automatically or manually controlled. Such lighting can also offer improved contrast ratio by wavelength selection. An input signal can be pulsed so as to allow spectral selectivity in an LED; chandelier lighting can be provided. Further, techniques/systems according to the present disclosure can allow the use of reflectance spectroscopy inside the eye. Improved light control may be provided during the air/fluid interface during surgical procedures, e.g., by utilizing a capacitance switch; one or more coatings (e.g., electrical contact) of the top of a cannula used for surgery; a pressure sensor; and/or temperature sensor based feedback.

Disposable systems according to the present disclosure can allow for (e.g., potentially unlimited) redundancy. For example, if one unit fails can open up another. Simple and smaller packaging allows the main vitrectomy control unit to be free of supporting a light source. This can allow flexibility in the design of future vitrectomy control units. Potentially allow clinic based surgery (surgery outside of the conventional operating room).

Handheld systems according to the present disclosure can include four primary components, as is described in greater detail below, including specifically selected/configured light sources. In addition to lights sources, various individual components/features useful for exemplary embodiments of the present disclosure can include a coupling system that can include one or more lens and filter configurations, and can allow a physician to select the wavelength of the light. Embodiments can also employ a fiber/coupling interface. The fiber/coupling interface can be configured so that the selected light is collimated/converged using a coupling system and then transmitted to (interfaced with) one or more optical fibers for improved coupling efficiency. A fiber output state/stage can also be used and can include one or more (possibly specialty) fibers for selective outputs. The fiber(s) can also be used as filters by using thin film deposited fibers.

FIG. 1 is a schematic view of a system level representation of a handheld illumination system 100 according to an embodiment of the present disclosure. System 100 can include a light source system, e.g., a LED source system 102, that can include a configuration of one or more light sources. The source system 102 can be connected to a coupling system 104 which can be connected to a fiber/coupling interface 106. The fiber/coupling interface 106 can be configured and arranged to provide light to a fiber output stage 108, as shown in the drawing.

Four primary components of the handheld system 100 can be incorporated in an injection molded housing structure, in exemplary embodiments. The energy supply component can be a DC source (e.g., a battery or rectified AC source) or a AC source and powers an electronic system. The electronic system, in turn, can consist of the microprocessor circuitry, which can be operational to provide a signal (e.g., current pulse) to the next component in the optical system, e.g., one or more light sources such as LEDs. In addition, the circuitry can include a converter/regulator, e.g., a boost converter. For battery-powered embodiments, a converter can be operable to step up the battery voltage to that required for light source(s), e.g., one or more LED sources.

The light source(s), e.g., one or more LEDs 102, can be run or operated on a suitable power supply, e.g., a current drive related to the discharge current of the battery. This allows a light source, e.g., and LED, to operate on an AC drive (e.g., from a wall plug) at a fixed/varied frequency. The coupling can be provided through the endo-probe component. As the system runs on pulse signal (e.g., a rectified AC signal) the power dissipated by the LED is a fraction of the steady state condition, allowing the temperature rise in the handle to be minimal. The parameters of the pulse signal (example: duty cycle etc.) can be changed in the design to achieve lower temperature dissipation. The intensity can be variable, which can allow a surgeon to control the optical output characteristics, e.g., during surgical procedures.

Continuing with the description of FIG. 1, suitable driver/driving parameters may be implemented for the power supplied to the light source(s) 102 of the handheld device. For example, a pulse rate can be implemented/designed that meets the minimum threshold for flicker fusion (human perception of a pulsed light as continuous), e.g., at greater than 60 Hz and less than 150 Hz, in exemplary embodiments. Any suitable duty cycle can be utilized. For example, a duty cycle can be used that varies from 1% to 90% for a pulsed scenario. Suitable current is used, depending on the type and configuration of light sources utilized, e.g., current can be used over a range that varies from 10 mA-1500 mA.

Figure 2:
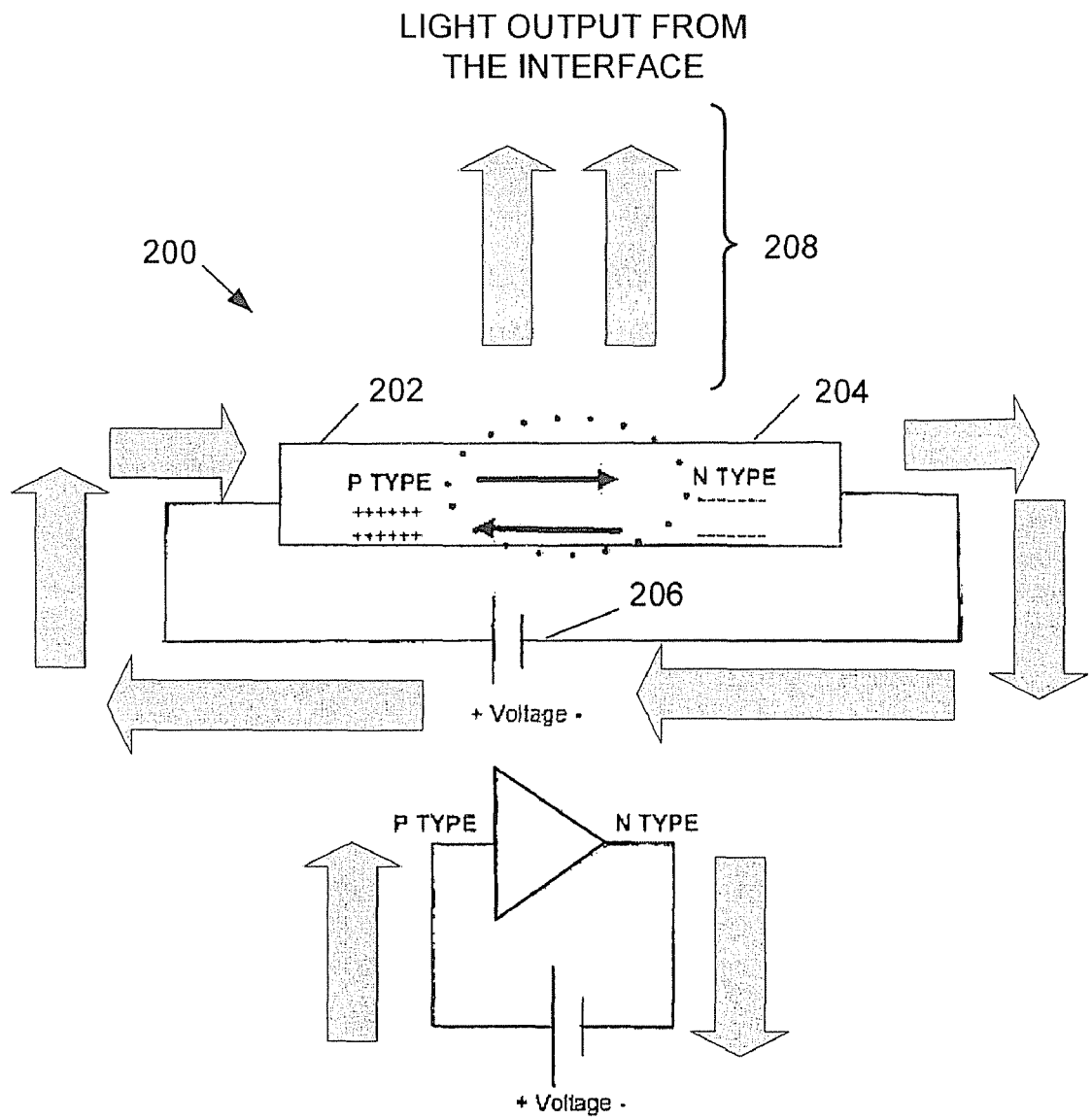
FIG. 2 is a schematic view of a light emitting diode.

FIG. 2 is a schematic of a light emitting diode 200, or LED, useful for use as a light source in exemplary embodiments of the present disclosure. As is known, LEDs are devices that convert electrical energy into optical energy. LED 200 is a semiconductor based diode (device) including a p-doped region 202 and a n-doped region 204. The principle behind an LED is as an electron in the conduction band recombines with a hole in the valence band; the electron makes a transition to a lower-lying energy state. This leads to the release of energy in an amount equal to the band-gap energy. In general, the energy is dissipated by phonons (heat) or photons (light). In an LED, this energy goes into emitted light energy.

When LED 200 is stimulated electrically as by a current (depicted by arrows) produced in response to an applied voltage 206, electrons and hole carriers in the p-n junction (depicted by elliptical region with opposed arrows) recombine, emitting photons as an incoherent narrow spectrum of light 208. This phenomenon is termed electroluminescence, where the color (UV, Visible, IR) of light depends on the type of the semiconductor material(s) used for the p-doped region 202 and n-doped region. Typically, the voltage applied to a LED is about 2.5V to about 4.0V, depending on the material(s) present.

As shown in FIG. 2, the LED emits optical power in proportion to the forward current through the diode interface. In addition, as LED 200 is a low voltage device, it has a longer life than traditional sources. The frequency response of LED's are ~10 MHz and the light can be collimated with a lens system (not shown). For exemplary embodiments, the voltage drop across LEDs utilized can be less than the specified forward voltage (for the particular LEDs), and the temperature of the handheld can be less than 40° C. The current source into the LED can be less than the specified current limit for each of the LEDs and the temperature of the handheld can be less than 40° C. Power can be supplied with a battery/battery pack contained within the hand piece, in exemplary embodiments.

According to exemplary embodiments of the preset disclosure, a novel optical handheld ophthalmic surgical instrument design for high efficiency illumination may be implemented as a wired illumination system or a wireless illumination system.

Figure 3:
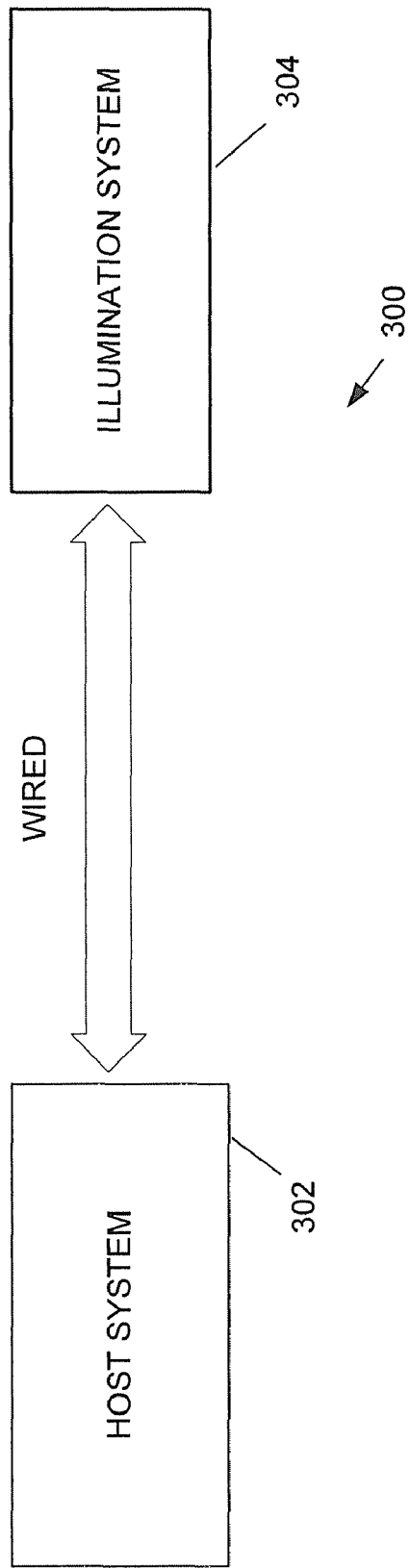
FIG. 3 depicts a system level representation of a wired illumination system according to an embodiment of the present disclosure, in which the host equipment and the handheld illumination system are configured to communicate through a wired protocol.

FIG. 3 shows a system level representation of a wired illumination system 300, where the host equipment/system 302 and the handheld illumination system 304 communicate through a wired protocol according to one embodiment of the disclosure. The host system 302 can include a command/control component, and can include current/voltage drivers with a computational platform. Additionally, the handheld system is an optical platform with an internal light source and coupling system.

Figure 4:
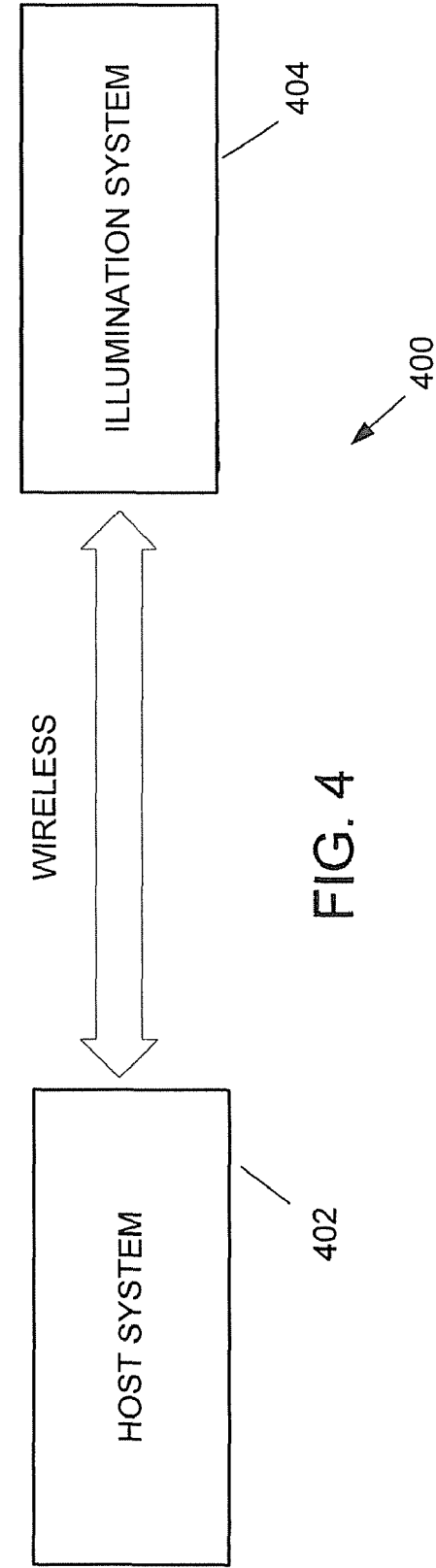
FIG. 4 depicts a system level representation of a wireless illumination system according to an embodiment of the present disclosure, in which the host and the handheld illumination system also are configured to communicate through a wireless protocol.
Figure 5:
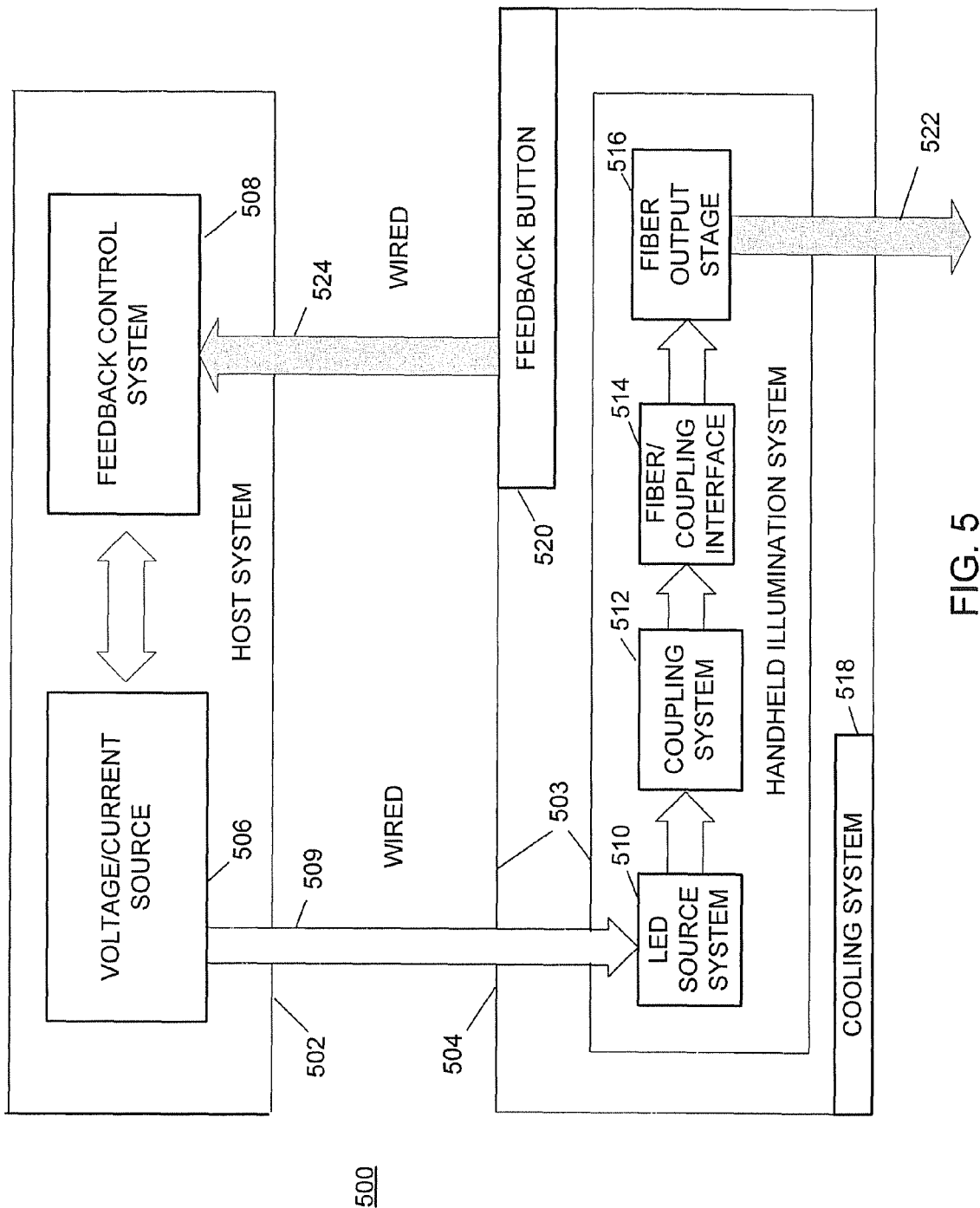
FIG. 5 depicts a block diagram representation of a wired illumination system according to one embodiment of the disclosure.
Figure 6:
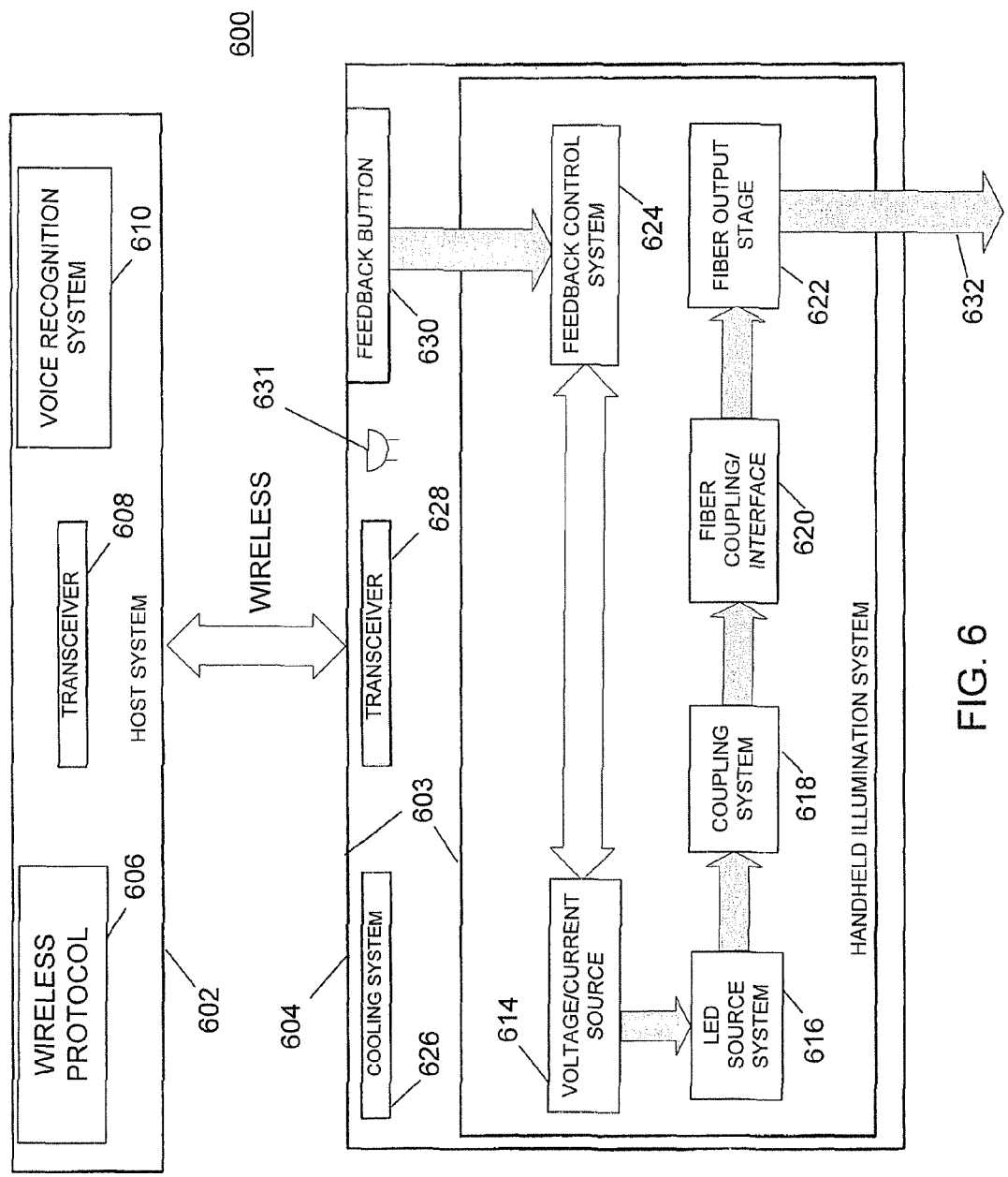
FIG. 6 depicts a block diagram representation of a wireless illumination system according to one embodiment of the disclosure.

FIG. 4 shows a system level representation of a wireless illumination system, in accordance with exemplary embodiments of the present disclosure. In system 400, a host system 402 can communicate with a handheld illumination system 404. According to an embodiment, the host system consists of the command/control only. The handheld system can be both an electrical and optical platform with an internal light source and coupling system. FIGS. 5 and 6 show details of the systems of FIGS. 3 and 4, respectively, in greater detail.

FIG. 5 is a block representation of a wired illumination system 500 according to an embodiment of the present disclosure. As shown in FIG. 5, the wired illumination 500 can include a host system 502 and a handheld illumination system 503.

The host system 502 can include a power supply, e.g., current/voltage source 506, that is operable to maintain and/or supply a required power to the handheld device, e.g., endoscope. Host system 502 can include a feedback control system 508. In FIG. 5, the arrows in the block diagram indicate the signal directionality. The power source 506 in the host system 502 supplies variable signal to the light source(s), e.g., embedded in the handheld system 503. Feedback control system 508 can be operable to communicate with the handheld system 503 either through a wired mechanism, as indicated in FIG. 5, or through a wireless connection, e.g., as indicated in FIG. 6. Handheld system 503 can also include a surrounding base or (docking) station 504, which can include components/systems such as cooling system 518, operational to cool the LED source system 510 or other portions of system 503 to a desired temperature, e.g., below 40 C, and/or feedback button 520.

The handheld illumination system 503 can include one or more light sources 510, which are preferably (though not necessarily) LEDs. Handheld illumination system 593 can include a coupling system 512. Fiber coupling system 512 can include suitable or desired lens and/or filter configurations and can allow a system operator (e.g., a physician) to select the wavelength of the light produced.

Handheld system 503 can further include a fiber/coupling interface 514. The fiber/coupling interface 514 can connect the coupling system 512 to the fiber output stage 516 and can be configured and arranged such that the selected light is collimated/converged using, e.g., an optical coupling system/assembly, and then interfaced with an optical fiber for improved coupling efficiency. A fiber output stage 516 can receive the light from the coupling system 512 and/or fiber/coupling interface 514 and can include one or more desired, e.g., specialty fibers, for selective outputs. The fiber(s) can also be used as filters by using thin film deposited fibers.

As shown, handheld system 503 can include a feedback triggering mechanism 520, e.g., button, switch, voice activated control, and the like. The feedback mechanism 520, e.g., button, can facilitate an operator's (e.g., a surgeon's) control of the light intensity at the output of the illuminated surgical instrument. For example, a surgeon could press button 520, in which event a signal would correspondingly be transmitted through a wire (wired connection indicated) to the feedback controller/control system 508. The feedback system 508 would then send a signal to the voltage/current source 506 leading so as to alter the power supplied to the light source(s), e.g., LED source system 510, to alter light output characteristic(s) such as intensity.

This feedback from the operator can allow or facilitate real time analysis and control and better viewing especially during an air fluid exchange during an operation. For further example, such feedback can be controlled such that the optical light intensity decreases/increases in and out of the eye chamber during a surgical procedure. A person of skill in the art should recognize that the input device used for the feedback may take any form known in the art, and is not limited to only buttons. For example, feedback may be in the form of voice commands.

The handheld portion, e.g., endo-scope, can be incorporated into and/or implemented with a mechanical design to reduce heat. In addition, a heat sink is used at the source end of the handheld system. According to the wired embodiment 500, the communication between the host 502 and the illumination system 503 is through a wired protocol.

FIG. 6 depicts a block diagram representation of a wireless illumination system 600 according to one embodiment of the present disclosure. As shown in FIG. 6, wireless illumination 600 can include a host system 602 and the handheld illumination system 603. The host system 602 can include a wireless protocol system 606 that includes of is linked with a trans-receiver (transceiver) system 608 to allow wireless communication with the handheld illumination system 603. Additionally, in exemplary embodiments, the host system 602 can include a voice activated protocol system 610. Protocol system 610 can include voice recognition software and hardware (e.g., voice recognition system), to permit a system operator (e.g., a surgeon) to communicate with the system 602/600. This allows voice commands in the application control of the system. The arrows in the block diagram indicate signal directionality.

The handheld illumination system 603 can include a power source 614 and feedback system 624 so that a handheld device, e.g., endo-probe, with the built-in lighting functionality can be self-powered and can communicate with feedback control/button 630. The handheld device 603 may further include a microphone for allowing entry of the voice commands by the surgeon. System 603 can include a power source (voltage/current source) 614, a light source system 616, e.g., a feedback control system 624, and a transceiver 628. According to the wireless embodiment of FIG. 6, the communication between the host system 602 and the illumination system 603 is through a wireless protocol. Handheld system 603 can also include a surrounding base or (docking) station 604, which can include components/systems such as cooling system 626, operational to cool the LED source system 616 or other portions of system 603 to a desired temperature, e.g., below 40 C, and/or feedback button 630.

As shown in FIG. 6, host system 602 can include a first transceiver 608, e.g., one adhering to a wireless communication protocol, and a voice recognition system 610 that can implement a voice activated protocol. Portable handpiece or handheld illumination system 603 can include a second transceiver 628 (for wireless communication with the host system 602), a power source 614, a feedback controller 624, and an illumination system emitting light 616 responsive to power received from the power source 614.

For system 600, a first user input device, e.g., feedback button 630, can control intensity of the light emitted by the illumination system 616. The first user input device 630 is operable to transmit to the feedback controller 624 a first signal based on a user-selected light intensity. The feedback controller 624 can transmit, in response to the first signal, a second signal to the power source 614 for altering the power provided by the power source 614 to the illumination system 616. The handpiece can also include a second user input device, e.g., sound sensor or microphone 631, for receiving voice data provided by the user. The voice data can wirelessly transmitted by the second transceiver 628 to the first transceiver 608 and processed by the voice recognition system 610 for storing or generating an output in response.

The handheld system 603 can be incorporated in an injection molded housing structure. An energy supply component/ system 614, e.g., a battery, can be included to provide power to the illumination system 616. The energy supply system 614 can include an electronic system that includes a microprocessor and related circuitry. The microprocessor/controller and related circuitry can or convert (e.g., rectify AC to pulsed DC) power to a desired condition, e.g., to regulate current pulses for the LEDs. In addition, the circuitry can consist of a converter, e.g., a boost, Buck, step down, step up, etc., to condition the power for the LEDs. A coupling can provided through a probe, e.g., an endo-probe, which can be coupled to the LED(s).

According to exemplary embodiments, the handheld illumination device may serve as potential light source for other illuminated instruments beside vitrectomy intraocular illumination, such as, for example, indirect opthalmoscope, direct opthalmoscope, slit lamp, and fundus camera.

Figure 7:
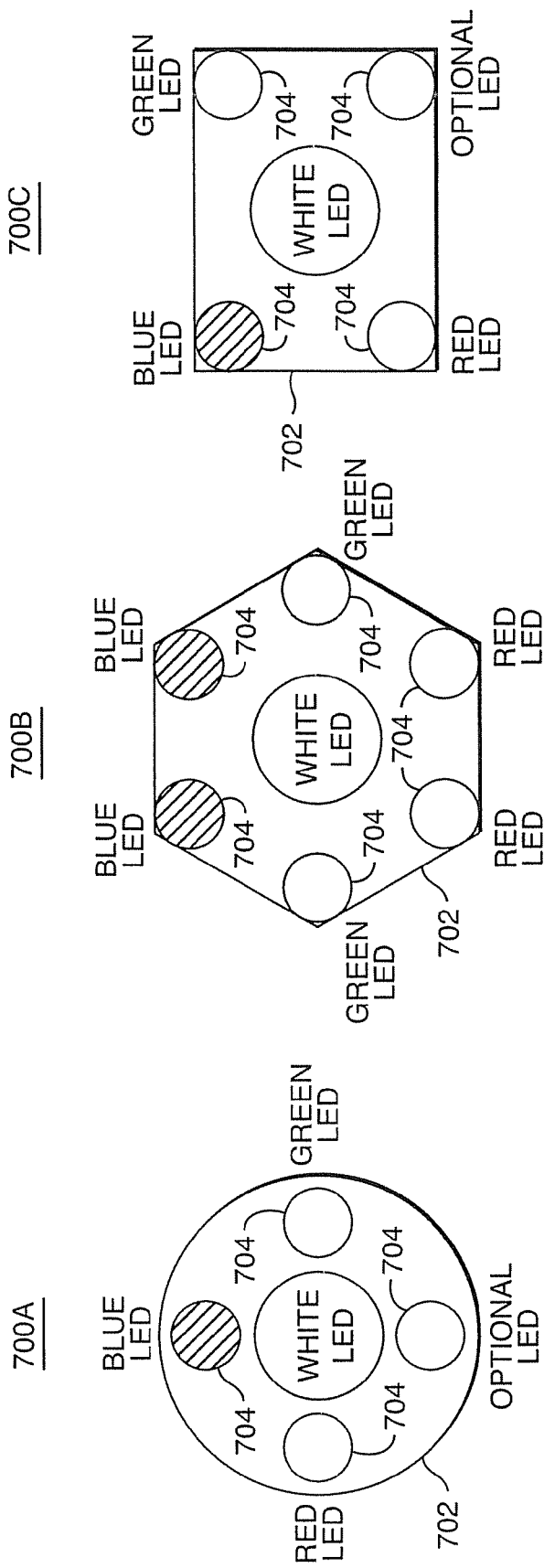
FIG. 7 depicts configurations of LEDs utilized as optical sources, with red, blue, green and white colors indicated.

Referring now to FIG. 7, light source configurations 700A-700C are depicted that utilize LEDs, with red, blue, green and white light outputs, in accordance with exemplary embodiments of the present disclosure. For configuration 700A-700C, base 702 can provide support for the LEDs 704. as shown. Base 702 can be made of any suitable material, e.g., plastic, metal, etc.

LEDs 704 that are selected (e.g., based on a user control command) as light sources can provide an optical signal/ output for illumination in a band of specific wavelengths. The different sources (red, green, blue, white, etc.) can be configured in a designated patterns for maximum light output efficiency. One of the advantages using this configuration is that by controlling the current to the LED, the output light can be tuned at various intensities. This can allow for better safety/ visualization and illumination that is tunable to individual cases and surgeons. In addition, the variation in light of different spectrum of the outputs of the LEDs 704 can allow for improved contrast ratios for surgical illumination.

In exemplary embodiments, e.g., those shown for FIG. 7, an illumination system according to the present disclosure can use multiple LED sources so as to provide an increased flux strength for illumination. Such multiple LEDs (or other sources) can be arranged in desired configurations, such as a star, hex, line, chandelier, etc. As for wavelengths of the optical output from the source(s), e.g., LEDs 704, the entire visible spectrum is usable. For LED sources, the optical intensities are easily tunable with the input current.

Figure 8:
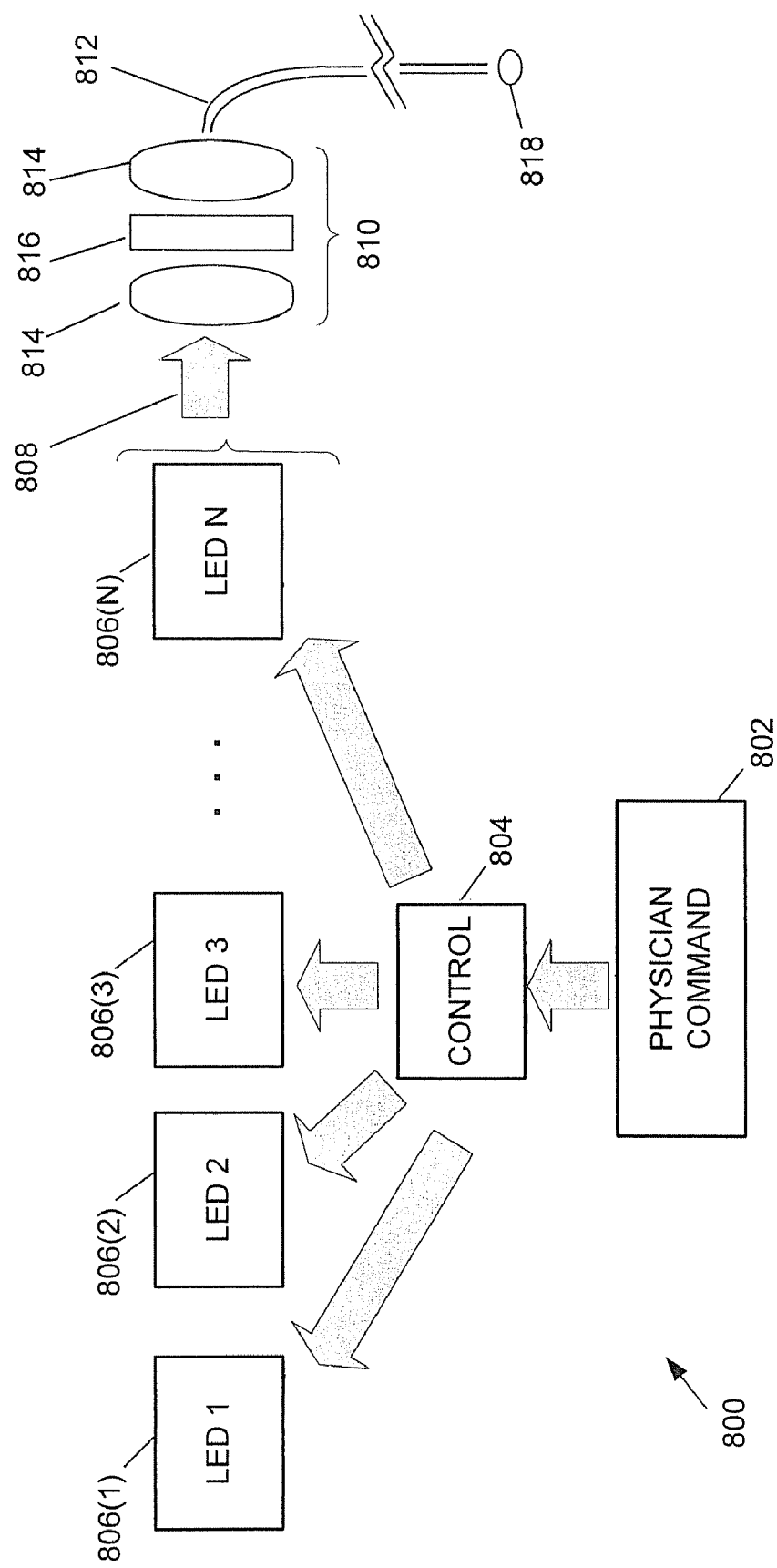
FIG. 8 depicts a diagrammatic view of application features an exemplary embodiment of feedback control for LED selectivity, according to the present disclosure.

FIG. 8 depicts a diagrammatic view representing the application feature of feedback control for LED selectivity according to an exemplary embodiment 800 of the present disclosure. As FIG. 8 shows, specific commands 802 control a control block 804 (e.g., feedback control) to activate one or more specific LEDs 806(1)-806(N) or a particular sub-combination of such LEDs 806(1)-806(N). The activation of specific LEDs and utilization of the light from the LED(s), can involve a combination of optical and electronic designs, e.g., as shown an described for FIGS. 1-7, and may be implemented either in a handheld or in the host system according to particular embodiments. The physicians command can be a feedback button/mechanism, e.g., as shown and described for FIGS. 5-6. In addition, feedback can allow the incorporation of a mechanism to determine/select one or more optical characteristics, e.g., how long an optical signal is ON (overall time and/or duty cycle), a particular wavelength or range used, and intensity.

Continuing with the description of FIG. 8, light produced by the LED(s) can be coupled, e.g., using a coupling system 810, into one or more optical fibers 812. This coupling system 810 can include a combination of one or more lenses 814 and/or one or more filters, which can serve to increase coupling efficiency of light output from the LED(s) 806(N) to the fiber(s) 812. In exemplary embodiments, fiber 812 can be placed through a casing (e.g., steel) to direct the light in a specific direction, e.g., to a desired portion of an endoscope. In exemplary embodiments, one or more specialized fibers can be used for specific filtering purposes and/or for desired applications. One skilled in the art, should appreciate that any suitable materials and/or shapes can be utilized for a lens 814 of coupling system 810. Further, one skilled in the art should appreciate that any suitable configuration (e.g., thin film, Fabry-Perot, etc.) and/or material can be used for a filter 816 of the coupling system 810. One or more lens 818 may be present at the tip of fiber 812 and may provide optional magnification, collimation, or focusing at the tip of the fiber 812.

Thus, from the previous description and review of the related drawings, it will be understood that embodiments and aspects of the present disclosure can provide various advantages relative to prior art techniques/systems.

The output light distribution of light sources utilized for embodiments of the present disclosure can be selected or designed for as desired. For example, an optical output can be Lambertian, "bat winged", Gaussian, etc. and suitable lenses and/or optical elements can be used with/for the light sources to give the desired output light distribution pattern. Further, a cooling system can be used to provide a cooling effect, allowing the illumination system to operate at low temperature(s), e.g., room temperature. Portability: light weight and small in size with no specialized cooling systems necessarily required for the handheld device (cooling may be implemented with the optical source system/components).

Feedback functionality can provide handheld control for physicians, and such ability may be provided by a convenient feedback button such as located on a handpiece/handheld device, probe, docking station for the handheld device, etc. Control of power current/voltage can be incorporated into the feedback control. Variable gain amplifiers can be incorporated in the power source, for exemplary embodiments, e.g., to provide dimming functionality. An automatic light in/out of the cannula feature may be implemented using the feedback button. A lens system utilized can be small and portable. Collimation and convergence as well as a variable spot size are also features that can be adjusted, e.g., by a surgeon operating a feedback controller/button.

Further advantages provided by embodiments of the present disclosure, can include the utilization of one or more combination of filters/attenuators. Also, optical fibers including special fibers with thin films deposited to eliminate harmful spectrum can be utilized. Different fiber configurations can be utilized, e.g., tapered, round, adiabatic, single-mode, multimode, graded index (GRIN), etc. Fiber optics used for embodiments may be selected and sized as desired, e.g., 50 µm-500 µm, and may be of multimode or single mode options/designs.

By utilizing LEDs as light sources, systems/techniques of the present disclosure can provide lighting that is largely if not entirely immune from or resistant to system vibrations. Lighting component lifetime can increase to thousands of hours, which is much higher than a normal (non-LED) light source. Further, LED-based light sources according to embodiments of the present disclosure can operate at lower temperatures, and therefore dissipate low heat, thereby eliminating complex heat sink systems. Costs related to lighting of the present disclosure techniques can be lower than that of prior art techniques, as costs for LED systems (including related driving power regulation circuitry) can be much less (e.g., exponentially less) expensive than a stand light source system because of the simple packaging. Additionally, LEDs are available in multiple colors/including high output efficiency, leading to selection of visible (and other) spectrums during surgical procedures, including those performed on the structure of the eye.

Moreover, LED-based lighting systems according to the present disclosure can offer improved surgeon controlled surgical instruments that can provide lighting that is either automatically or manually controlled. Such lighting can also offer improved contrast ratio by wavelength selection. An input signal can be pulsed so as to allow spectral selectivity in an LED; chandelier lighting can be provided. Further, techniques/systems according to the present disclosure can allow the use of reflectance spectroscopy inside the eye. Improved light control may be provided during the air/fluid interface during surgical procedures.

Further, embodiments of the present disclosure can allow handheld illumination device to allow novel application outside of the operating room and independent of an integrated vitrectomy control unit or an expensive light source box, e.g., use in a clinic; and/or potential light source for other illuminated instruments beside vitrectomy intraocular illumination, such as for an indirect opthalmoscope, a direct opthalmoscope, a slit lamp, a fundus camera, and the like.

Although the present disclosure has been described in certain specific embodiments, those skilled in the art will have no difficulty devising variations to the described embodiment which in no way depart from the scope and spirit of the present disclosure. For example, although the illumination system according to the previously described embodiments have generally been in the context of utilizing LEDs, a person of skill in the art should recognize that other types of light sources may also be used in addition or in lieu of LEDs. Furthermore, in addition or in lieu of manual adjustment of the light intensity via the feedback buttons, sensors may also be incorporated into the handpiece for sensing different types of lighting requirements for automatically adjusting the light intensity based on the sensed lighting requirements.

Furthermore, to those skilled in the various arts, the disclosure itself herein will suggest solutions to other tasks and adaptations for other applications. It is the Applicants' intention to cover all such uses of the disclosure and those changes and modifications which could be made to the embodiments of the disclosure herein chosen for the purpose of disclosure without departing from the spirit and scope of the disclosure. Thus, the present embodiments of the disclosure should be considered in all respects as illustrative and not restrictive.

What is claimed is:

1. An ophthalmic surgical illumination system comprising:
   a power source configured and arranged to produce a power output of a desired power;
   a portable ophthalmic surgical handpiece configured for intraocular illumination including:
   an illumination system configured and arranged to emit light in response to power received from the power source, the illumination system comprising a plurality of light emitting diodes;
   a microprocessor configured to generate a pulse signal for sending to the plurality of light emitting diodes, wherein the pulse signal is configured to maintain the portable ophthalmic surgical handpiece at a desired temperature by reducing heat dissipation by the plurality of light emitting diodes;
   a temperature sensor connected to the microprocessor, the temperature sensor configured to provide feedback to the microprocessor to maintain the portable ophthalmic surgical handpiece at the desired temperature;
   a coupling system configured and arranged to select a wavelength range of the light from the illumination system;
   a coupling interface configured and arranged to couple light from the coupling system into one or more optical fibers; and a fiber output stage including one or more optical fibers and configured and arranged to deliver light from the coupling interface to a surgical site;

wherein the plurality of light emitting diodes comprises a first light emitting diode configured to emit white light and a second light emitting diode configured to emit color light to enerate contrast ratios for surgical illumination.

2. The system of claim 1, further comprising:
a feedback controller configured and arranged to adjust the power output of the power source; and
a user input device for controlling intensity of light emitted by the illumination system, the user input device transmitting to the feedback controller a first signal based on a user-selected light intensity, the feedback controller transmitting in response to the first signal, a second signal to the power source for altering the power output provided by the power source to the illumination system.

3. The system of claim 1, wherein the power source is disposed in the portable handpiece.

4. The system of claim 2, further comprising a sound sensor disposed within the portable handpiece and configured and arranged to detect spoken signals, wherein the sound sensor is configured and arranged to send an input signal to the feedback controller.

5. The system of claim 1, wherein the plurality of light emitting diodes comprises one or more LEDs operable to produce a green light output.

6. The system of claim 1, wherein the plurality of light emitting diodes comprises one or more LEDs operable to produce a blue light output.

7. The system of claim 1, wherein the plurality of light emitting diodes comprises one or more LEDs operable to produce a red light output.

8. The system of claim 1, wherein the plurality of light emitting diodes comprises two or more LEDs operable to produce a white light output.

9. An ophthalmic surgical illumination system comprising:
a host system with a power source and a controller in communication with a handheld ophthalmic surgical illuminator having a microprocessor and a control mechanism communicating with the host system; and wherein the handheld ophthalmic surgical illuminator comprises a plurality of light emitting diodes configured to emit light responsive to power received from the host system;

wherein the microprocessor is configured to generate a pulse sinal for sending to the plurality of light emitting diodes, wherein the pulse signal is configured to maintain the handheld ophthalmic surgical illuminator at a desired temperature by reducing heat dissipation by the plurality of light emitting diodes; and wherein the plurality of light emitting diodes comprises a first light emitting diode configured to emit white light and a second light emitting diode configured to emit colored light and a coupling system within the handheld ophthalmic surgical illuminator to combine substantially white light from the first light emitting diode with colored light from the second light emitting diode to produce a tinted light.

10. The system of claim 9, wherein the handheld ophthalmic surgical illuminator includes an input device for controlling the power source on/off state of the emitted light and intensity of the emitted light of the handheld ophthalmic surgical illuminator.

11. The system of claim 10, wherein the input device comprises a user input device configured and arranged to transmit to the controller a first signal to turn on/off based on user selected power state, and wherein the controller is configured and arranged to transmit a second signal to the power source to initiate/terminate power to the plurality of light emitting diodes.

12. The system of claim 11, wherein the user input device is configured and arranged to transmit a third signal to the controller to change the intensity of the emitted light, and the controller is configured and arranged to transmit a fourth signal to the power source to alter the power to the handheld ophthalmic surgical illuminator.

13. The system of claim 12, wherein the user input device is configured and arranged to transmit a fifth signal to the controller to control first intensity and spectral range of the emitted light.

14. The system of claim 1, wherein the desired temperature is less than 40 degrees C.

15. The system of claim 9, wherein the desired temperature is less than 40 degrees C.

* * * * *

UNITED STATES PATENT AND TRADEMARK OFFICE
CERTIFICATE OF CORRECTION

| | | |
|---|---|---|
| PATENT NO. | : 8,172,834 B2 | |
| APPLICATION NO. | : 12/237110 | |
| DATED | : May 8, 2012 | |
| INVENTOR(S) | : Prashant R. Bhadri et al. | |

It is certified that error appears in the above-identified patent and that said Letters Patent is hereby corrected as shown below:

At column 2, line 3-4, please change "handpiece an" to --handpiece can--.

At column 2, line 40, please change "opthalmoscope," to --ophthalmoscope,--.

At column 2, line 41, change "opthalmoscope," to --ophthalmoscope,--.

At column 2, line 42, please change "of the of" to --of the--.

At column 8, line 8, please change "opthalmoscope," to --ophthalmoscope,--.

At column 8, line 9, please change "opthalmoscope," to --ophthalmoscope,--.

At column 10, line 16, please change "opthalmoscope," to --ophthalmoscope,--.

At column 10, line 16-17, please change "opthalmoscope," to --ophthalmoscope,--.

At column 11, line 7, In Claim 1, please change "enerate" to --generate--.

At column 12, line 6, In Claim 9, please change "sinal" to --signal--.

Signed and Sealed this
Eleventh Day of September, 2012

David J. Kappos
*Director of the United States Patent and Trademark Office*